United States Patent
Laroche et al.

(10) Patent No.: US 10,723,677 B2
(45) Date of Patent: *Jul. 28, 2020

(54) ZEOLITIC GRANULAR MATERIAL HAVING A CONNECTED STRUCTURE

(71) Applicants: CECA S.A., Colombes (FR); IFP ENERGIES NOUVELLES, Rueil-malmaison (FR)

(72) Inventors: Catherine Laroche, Vernaison (FR); Ludivine Bouvier, Orthez (FR); Philibert Leflaive, Mions (FR); Cecile Lutz, Gan (FR); Anne-Sophie Gay, Saint-Etienne (FR); Florent Moreau, Lyons (FR)

(73) Assignees: ARKEMA FRANCE, Colombes (FR); IFP ENERGIES NOUVELLES, Rueil-Malmaison (FR)

( * ) Notice: Subject to any disclaimer, the term of this patent is extended or adjusted under 35 U.S.C. 154(b) by 247 days.

This patent is subject to a terminal disclaimer.

(21) Appl. No.: 15/037,896

(22) PCT Filed: Nov. 20, 2014

(86) PCT No.: PCT/EP2014/075191
§ 371 (c)(1),
(2) Date: May 19, 2016

(87) PCT Pub. No.: WO2015/075140
PCT Pub. Date: May 28, 2015

(65) Prior Publication Data
US 2016/0289146 A1 Oct. 6, 2016

(30) Foreign Application Priority Data
Nov. 20, 2013 (FR) ..................................... 13 61380

(51) Int. Cl.
*B01J 20/18* (2006.01)
*C07C 7/13* (2006.01)
*B01J 20/28* (2006.01)
*B01J 20/30* (2006.01)
*C07C 29/76* (2006.01)
*C07C 15/08* (2006.01)
*C07C 37/82* (2006.01)
*C10G 25/03* (2006.01)
*B01J 20/12* (2006.01)

(52) U.S. Cl.
CPC .................. *C07C 7/13* (2013.01); *B01J 20/12* (2013.01); *B01J 20/18* (2013.01); *B01J 20/183* (2013.01); *B01J 20/2803* (2013.01); *B01J 20/28004* (2013.01); *B01J 20/2808* (2013.01); *B01J 20/28011* (2013.01); *B01J 20/28016* (2013.01); *B01J 20/28069* (2013.01); *B01J 20/28083* (2013.01); *B01J 20/28085* (2013.01); *B01J 20/28088* (2013.01); *B01J 20/28092* (2013.01); *B01J 20/3007* (2013.01); *B01J 20/3021* (2013.01); *B01J 20/3028* (2013.01); *B01J 20/3042* (2013.01); *B01J 20/3078* (2013.01); *B01J 20/3085* (2013.01); *C07C 15/08* (2013.01); *C07C 29/76* (2013.01); *C07C 37/82* (2013.01); *C10G 25/03* (2013.01); *C10G 2300/1096* (2013.01); *C10G 2400/30* (2013.01)

(58) Field of Classification Search
CPC ............ B01J 20/28083; B01J 20/28069; B01J 20/2808; B01J 20/28004; B01J 20/28011; B01J 20/28088; B01J 20/28085; B01J 20/28092; B01J 20/28016; B01J 20/2803; B01J 20/12; B01J 20/18; B01J 20/183; B01J 20/3007; B01J 20/3021; B01J 20/3078; B01J 20/3042; B01J 20/3085; B01J 20/3028; C07C 7/13; C07C 37/82; C07C 29/76; C07C 15/08; C07C 15/067; C10G 25/03; C10G 2300/1096; C10G 2400/30
USPC ..... 502/60, 64, 70, 400, 405, 407, 414, 415; 210/660, 661; 585/804, 805, 820, 828
See application file for complete search history.

(56) References Cited

U.S. PATENT DOCUMENTS 6,264,881 B1 * 7/2001 Plee ....................... B01J 20/183
264/628
6,514,317 B2 * 2/2003 Hirano ................... B01D 53/02
95/106

(Continued)

FOREIGN PATENT DOCUMENTS

WO 2000000287 1/2000
WO 2008009845 1/2008

(Continued)

OTHER PUBLICATIONS

Petrov et al., "Synthesis of zeolite A: A review", Scientific, 51, 2012, pp. 30-35.*

(Continued)

*Primary Examiner* — Elizabeth D Wood
(74) *Attorney, Agent, or Firm* — RatnerPrestia

(57) ABSTRACT

The present invention relates to a zeolitic granular material having a connected zeolitic structure across the entire volume thereof, having high mechanical resistance to crushing in the bed, and optimised material transfer in the macromesopores. The invention also relates to the method for preparing said zeolitic granular material, as well as to the use thereof as an adsorbent material in co-current or counter-current liquid phase separation methods, typically in a simulated mobile bed.

15 Claims, 2 Drawing Sheets

(56) References Cited

U.S. PATENT DOCUMENTS

Figure 1A:
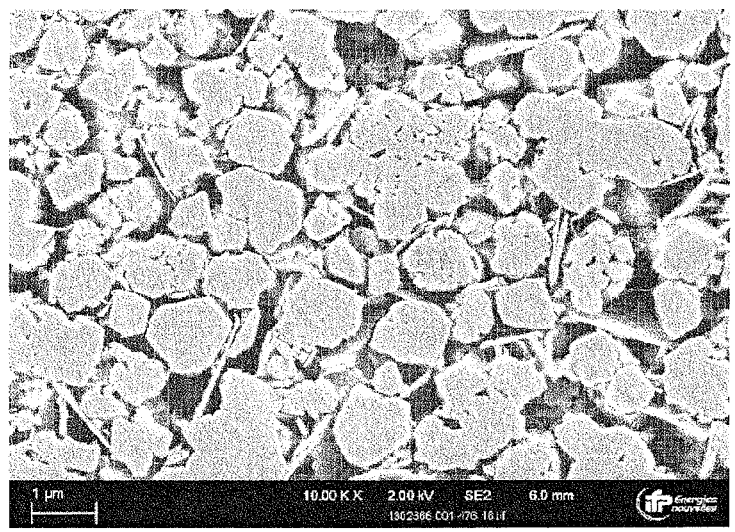

| | | | | |
|---|---|---|---|---|
| 6,537,348 B1* | 3/2003 | Hirano | ............... | B01D 53/02 95/114 |
| 6,884,918 B1* | 4/2005 | Plee | ............... | B01J 20/183 585/820 |
| 7,935,177 B2* | 5/2011 | Lutz | ............... | B01J 20/18 95/129 |
| 8,282,900 B2* | 10/2012 | Hirano | ............... | B01D 53/02 423/240 R |
| 9,707,539 B2* | 7/2017 | Bats | ............... | B01J 20/186 |
| 2001/0045160 A1* | 11/2001 | Hirano | ............... | B01D 53/02 95/96 |
| 2002/0170436 A1* | 11/2002 | Keefer | ............... | B01J 20/183 96/121 |
| 2005/0170947 A1* | 8/2005 | Plee | ............... | B01J 20/183 502/64 |
| 2008/0156190 A1* | 7/2008 | Lutz | ............... | B01J 20/18 95/148 |
| 2010/0113854 A1* | 5/2010 | Bouvier | ............... | B01J 20/183 585/828 |
| 2010/0196213 A1 | 8/2010 | Lutz | | |
| 2011/0104494 A1 | 5/2011 | Brandt | | |
| 2011/0105301 A1 | 5/2011 | Wang | | |
| 2011/0124942 A1 | 5/2011 | Bouvier | | |
| 2011/0184165 A1* | 7/2011 | Bouvier | ............... | B01J 20/18 536/127 |
| 2012/0093715 A1 | 4/2012 | Wang | | |
| 2013/0012377 A1 | 1/2013 | Suh | | |
| 2013/0052126 A1 | 2/2013 | Wang | | |
| 2015/0306565 A1* | 10/2015 | Bouvier | ............... | B01J 20/18 568/758 |

FOREIGN PATENT DOCUMENTS

| | | | |
|---|---|---|---|
| WO | 2008152319 | 12/2008 | |
| WO | 2009081023 | 7/2009 | |
| WO | 2009081024 | 7/2009 | |
| WO | WO 2014/177567 | * 11/2014 | |

OTHER PUBLICATIONS

International Search Reporta and Written Opinion for International Application No. PCT/EP2014/07519, dated Aug. 1, 2015, 15 pages.

European Communication Pursuant to Article 94(3) for European Application No. 14 800 077.1, dated May 18, 2020, 11 pages.

* cited by examiner

ZEOLITIC GRANULAR MATERIAL HAVING A CONNECTED STRUCTURE

CROSS-REFERENCE TO RELATED APPLICATIONS

This is the national phase of International Application No. PCT/EP2014/075191, filed 20 Nov. 2014, which claims priority from French Application No. 1361380 filed 20 Nov. 2013. The disclosure of each of these applications is incorporated herein by reference in its entirety for all purposes.

FIELD OF THE INVENTION

The present invention relates to the field of adsorbents with zeolitic structure and more particularly to the field of adsorbents with zeolitic structure in the form of agglomerates. The present invention also relates to the synthesis of said agglomerates with zeolitic structure, and also to the uses thereof for separating gaseous or liquid mixtures.

DISCUSSION OF THE RELATED ART

The synthesis of zeolites leads to crystals, generally in powder form, whose use at the industrial scale is particularly difficult. Specifically, it is now known how to synthesize zeolite crystals with sizes ranging from a few nanometers to a few micrometers, these sizes being required to give the zeolites optimum adsorption capacities. However, there are many drawbacks associated with these small crystals, among which drawbacks mention may be made of the difficulty in handling pulverulent powder and the substantial pressure losses during their uses.

In order to overcome these drawbacks, it has thus been proposed to use agglomerated forms of these crystals, for example in the form of grains, yarns, beads or other agglomerated forms. The manufacture of such agglomerates from zeolite crystals in powder form is now well known, and the scientific literature and the patent literature provide numerous examples of preparation of zeolite agglomerates, especially by extrusion, pelletizing and other agglomeration techniques known to those skilled in the art.

These agglomerates are usually in sizes of the order of a few tens of micrometers, or even a few hundred micrometers, or even a few millimeters, and do not have the drawbacks inherent in pulverulent materials such as the zeolite crystals defined previously.

These agglomerates, whether in the form of platelets, beads, extrudates or other forms, generally consist of zeolite crystals, which constitute the active element (as regards the adsorption), and of an agglomeration binder.

This agglomeration binder is intended to ensure the cohesion of the crystals to each other in the agglomerated structure, but must also provide sufficient mechanical strength to said agglomerates so as to avoid, or at the very least minimize, the risks of fractures, cracks or breaks that might occur during their industrial uses during which the agglomerates are subjected to numerous stresses, such as vibrations, large and/or frequent variations in pressure, movements and the like. It is thus very important for the zeolite agglomerates subjected to these various stresses to remain cohesive and not to generate pulverulent fine particles leading to the abovementioned drawbacks.

Moreover, the important factors that influence the performance of a process of separation by adsorption especially include the adsorption selectivity, the adsorption capacity and the material transfer kinetics which define the rates of adsorption and desorption of various compounds. The adsorbent must thus have good material transfer properties so as to ensure a sufficient number of theoretical plates to achieve efficient separation of the species in the mixture, as indicated by Ruthven in the publication entitled *Principles of Adsorption and Adsorption Processes*, John Wiley & Sons, (1984), pages 326 and 407.

In the case of a zeolite adsorbent in agglomerated form, the overall material transfer depends on the addition of the intra-crystalline diffusional resistance and of the diffusional resistance between crystals (see Ruthven, ibid. p. 243). The intra-crystalline diffusional resistance is proportional to the square of the radii of the crystals and inversely proportional to the intra-crystalline diffusivity of the molecules to be separated by adsorption. The diffusional resistance between crystals (also known as the macroporous resistance) is itself proportional to the square of the radii of the agglomerates and inversely proportional to the diffusivity of the molecules to be separated in the macropores.

It is thus sought to minimize the diameter of the zeolite crystals and/or to minimize the diameter of the agglomerates so as to improve the material transfer. Such reduced-size agglomerates, optionally comprising reduced-size crystals, however prove to be more fragile, and it then becomes necessary to increase the content of agglomeration binder in order to reinforce the cohesion of the crystals to each other in the agglomerate. However, increasing the content of agglomeration binder, which is inert with respect to adsorption, proportionately reduces the adsorption capacities of the agglomerates relative to zeolite crystals used alone, in the form of non-agglomerated powder.

A need has thus appeared to create zeolite adsorbents in agglomerated form combining good material transfer properties, a size compatible with its use at the industrial scale, typically between 0.1 mm and 1 mm, and very great mechanical strength, while at the same time conserving the adsorption properties required for their uses.

The prior art proposes several possibilities, among which a first possibility consists in preparing zeolite monocrystals that are large enough to be able to be handled directly in an industrial separation process. The preparation of large-sized zeolite monocrystals has been discussed in the literature. In particular, Qiu et al. (*Micropor. Mesopor. Mater.*, 21 (4-6), (1998), 245-251) indicate that zeolite monocrystals of faujasite structure with a size ranging up to 150 μm may be obtained in the presence of nucleation inhibitors and by using reagents of very high purity. Besides the difficulties that may be envisaged for the industrialization of this type of synthesis, it appears impossible to synthesize zeolite crystals with a size of between 0.1 mm and 1 mm which would typically be the size required for use in an industrial process, especially in liquid phase, without major implementation difficulties. Furthermore, since the macroporosity and mesoporosity of these materials are virtually zero, it appears very probable to observe very poor transportation of the compounds to be adsorbed/separated in the zeolite phase over a characteristic distance corresponding to the size of the agglomerate, or of the zeolite adsorbent in crystalline monolith form.

Patent applications US 2012/0093715 and US 2013/0052126 teach that monolithic zeolite structures may be formed with a structure of hierarchical porosity. The method proposed consists in forming a gel of zeolite precursor by hydrolysis. This gel is heated to a sufficiently high temperature and for long enough to crystallize and agglomerate the gel into a monolithic zeolite structure. The addition of a polymer to the reaction medium leads to the production of monolithic zeolite structures with a structure having hierarchical porosity.

Nevertheless, the monolithic zeolite structures described in these patent applications have a macroporosity and a mesoporosity, measured by mercury intrusion, which are low in the case where no organic structuring agent is used. It may thus be feared that, as in the case of monocrystals, the material transfer within the structure is then relatively mediocre. In the case where a polymeric organic agent is used, and besides the fact that a step of shrinkage of the organic agent is necessary, the solid has, in contrast, a very high porosity.

It may thus be feared that the mechanical strength of the material is relatively poor and that the adsorption capacity per unit bed volume of adsorbent is also low.

Patent application WO 2000/000287 also describes the production of mineral macrostructures whose porosity is created and controlled by the use of an organic resin which must be removed at the end of the process.

The above patent applications also all appear to be uneconomical, since the processes detailed require the use of organic agents that involve an additional cost and an additional removal step during the manufacturing process.

The production of 13X zeolite monoliths with hierarchical porosity is also described by Akhtar and Bergström (*J. Am. Chem. Soc.*, 94(1), (2001), 92-98). The authors show that the molding of colloidal suspensions of 13X zeolite powder concentrated and stabilized by addition of polyethylene glycol makes it possible to obtain materials known as green bodies, which, after a "flash" heat treatment at 800° C., lead to monoliths with hierarchical porosity, said monoliths being strong and having a $CO_2$ adsorption capacity close to that of the corresponding powder (zeolite crystals).

These relatively large materials (the characteristic size is indicated as being greater than 10 mm) obtained via the described process (molding) appear to be indeed suitable for gas-phase processes, the essence of the material transfer resistance then being in the micropores. However, it may be doubted that such materials are very efficient for liquid-phase applications or the material transfer in the macro-mesopores must also be optimized.

There is consequently still a need for nonpulverulent zeolitic adsorbent materials, of high mechanical strength and whose adsorption capacities in gas and/or liquid phase, preferably in liquid phase, are greatly improved.

SUMMARY OF THE INVENTION

Thus, a first object of the present invention is to provide a zeolitic granular material composed of a zeolite structure percolating over the entire volume of the material, which has high mechanical strength, optimized material transfer in the macropores and mesopores, which is readily industrializable and with relatively low manufacturing costs. Other objects will appear in the light of the description of the present invention that follows.

The inventors have succeeded in preparing such a zeolitic granular material that satisfies the various abovementioned objects and makes it possible to overcome all or at least some of the drawbacks and defects of the adsorbents known in the prior art.

Thus, and according to a first aspect, the subject of the present invention is a zeolitic granular material with high mechanical strength, having a percolating zeolite structure, i.e. forming a connected assembly over the entire volume of said material.

More precisely, the invention relates to a small-sized zeolitic granular material, typically between 0.1 mm and 1 mm, limits inclusive, of percolating structure, thus ensuring optimized transport of the molecules that it is desired to separate by adsorption, in liquid phase or in gas phase, preferably in liquid phase, within the macropores and mesopores of the material and within the zeolite phase, and having a particular structure that affords very high mechanical strength.

The zeolitic granular material according to the present invention has a high mechanical bulk crushing strength (BCS), measured by the Shell method series SMS1471-74 adapted for agglomerates smaller than 1.6 mm, as described later in the description. The BCS of the zeolitic granular material of the invention is generally greater than or equal to 1.0 MPa, more generally greater than or equal to 1.5 MPa, preferably greater than or equal to 2.0 MPa, typically greater than or equal to 2.1 MPa.

Figure 1B:
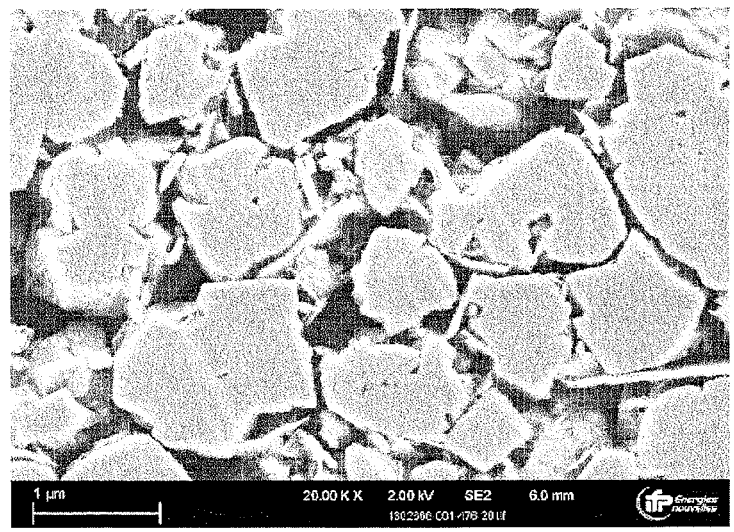
Figure 2A:
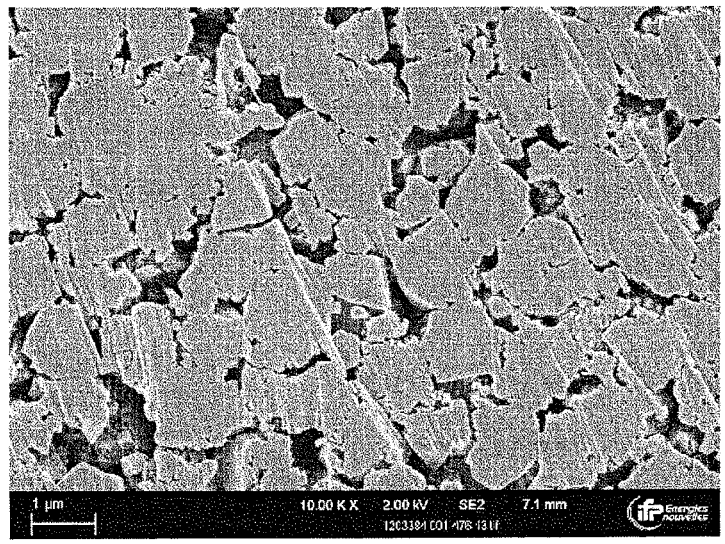
Figure 2B:
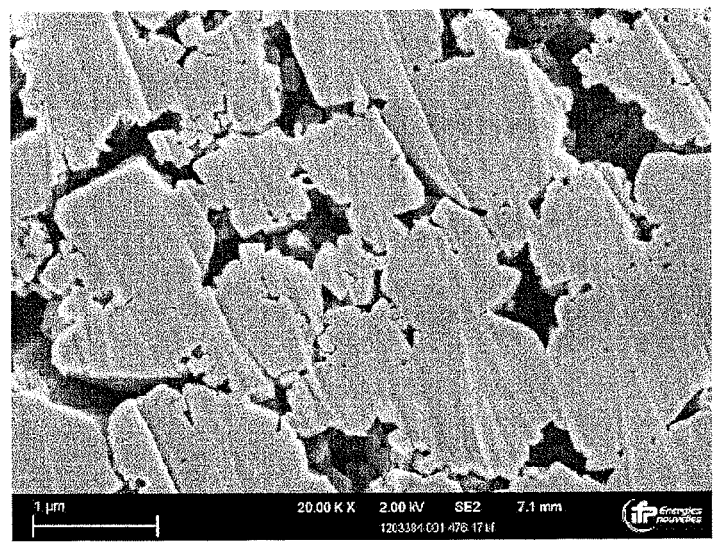

The attached figures are commented on below:

FIG. 1*a*: non-connected zeolitic granular material corresponding to Example 1, magnification 5000;

FIG. 1*b*: non-connected zeolitic granular material corresponding to Example 1, magnification 10 000;

FIG. 2*a*: connected zeolitic granular material corresponding to Example 2, magnification 5000;

FIG. 2*b*: connected zeolitic granular material corresponding to Example 2, magnification 10 000.

DETAILED DESCRIPTION OF CERTAIN EMBODIMENTS OF THE INVENTION

The term "assembly connected over the entire volume of said material" means a three-dimensionally connected structure, preferably three-dimensionally connected by arcs, i.e. any pair of points in the zeolite structure is connected via a path, the term "path" being taken in its mathematical definition used in topology, thus increasing the density of the network of "force chains" supporting the mechanical stresses as a whole.

For the purposes of the invention, several polished sections are prepared, and are examined with a scanning electron microscope (SEM). Ten images are taken on the various polished sections, with a magnification of between 5000 and 10 000, and the surface forming a connected assembly is evaluated by image analysis, or any other suitable means, for each of the ten images. The zeolitic granular material of the invention is considered as being an "assembly connected over the entire volume of said material" when the proportion (mean of the ten images) of connected surface represents at least 50%, preferably at least 70%, more preferably at least 80% of the surface occupied by the material on each image.

According to a preferred aspect of the invention, the zeolitic granular material has open macroporosity. The term "open macroporosity" means porosity that is accessible from the outer surface of the granular material, such a porosity being able to be characterized via the "mercury intrusion" technique, which is a porosimetry technique that is well known to those skilled in the art.

In the description of the invention, the term "size" means the number-average diameter of an object, or its number-average largest dimension when it is not spherical. The zeolitic granular material of the invention has a size typically of between 0.1 mm and 1 mm, preferably between 0.2 mm and 1 mm, in particular between 0.3 mm and 0.8 mm and more generally between 0.4 mm and 0.6 mm, limits inclusive.

The zeolitic granular material of the invention comprises macropores, mesopores and micropores. The term "macropores" means pores whose aperture is greater than 50 nm, preferably between 50 nm and 400 nm, more preferably between 50 nm and 300 nm. The term "mesopores" means pores whose aperture is between 2 nm and 50 nm, limits not inclusive. The term "micropores" means pores whose aperture is less than 2 nm, typically strictly greater than 0 and less than or equal to 2 nm.

The granular material according to the present invention is a zeolite material, indicating that it comprises at least one zeolite chosen from zeolites of FAU structure, chosen especially from zeolites LSX, MSX, X, Y and from zeolites of structure EMT, LTA or MFI. Among these zeolites, the ones that are preferred are those chosen from zeolites LSX, MSX and X, and more preferably zeolite X, without excluding mixtures of zeolites X with one or more of the other zeolites listed above.

As a general rule, the zeolitic granular material of the invention comprises more than 94% by weight of zeolite(s), preferably between 96% and 98% by weight of zeolite(s), limits inclusive, relative to the total weight of the zeolite granular material.

According to a preferred embodiment, the zeolite(s) is (are) in the form of crystals with a size generally between 10 nm and 1500 nm, preferably between 100 nm and 1200 nm, more preferably between 200 nm and 1100 nm and most particularly preferably between 400 nm and 1000 nm, limits inclusive.

The zeolitic granular material of the present invention is also characterized by a specific pore distribution, in which the macropore and mesopore volumes are measured by mercury intrusion and the micropore volume is measured by nitrogen adsorption. The term "pore distribution" means the distribution of the pore volume as a function of the pore diameter. Moreover, in the description of the present invention, the term "Vma" denotes the macropore volume, the term "Vme" denotes the mesopore volume and the term "Vmi" denotes the micropore volume. "Vg" represents the total volume of the granular material.

According to a most particularly preferred embodiment of the present invention, the pore distribution of the zeolite granular material satisfies the following inequalities 1), 2) and 3):

$$\frac{Vme}{Vme + Vma} \leq 0.1, \quad 1)$$

preferably $$0.01 \leq \frac{Vme}{Vme + Vma} \leq 0.1,$$

more preferentially $$0.01 \leq \frac{Vme}{Vme + Vma} \leq 0.06;$$

$$0.4 \leq \frac{Vmi}{Vma + Vme + Vmi}, \quad 2)$$

preferably $$0.4 \leq \frac{Vmi}{Vma + Vme + Vmi} \leq 0.6,$$

more preferably $$0.45 \leq \frac{Vmi}{Vma + Vme + Vmi} \leq 0.55;$$

and $$0.25 \leq \frac{Vma + Vme}{Vg} \leq 0.35. \quad 3)$$

The specific pore distribution of the zeolitic granular material of the invention describes a material whose micropore, mesopore and macropore volumes are adjusted, according to the ratios defined previously, so as to allow efficient transport, from the exterior of the granular material to the zeolitic structure, of the compounds to be separated by adsorption, while at the same time conserving optimum adsorption capacity.

The combination of this specific pore distribution with the connected nature of the zeolite structure makes it possible to give said material, on the one hand, very good liquid or gas separation properties and, on the other hand, very good mechanical strength, by virtue of the existence of bridges (or arches) between the crystals.

Specifically, it is known that when an assembly of crystals is solicited, by compression, or alternatively by exerting a shear, the distribution of the forces resulting therefrom within this assembly is very heterogeneous. Specifically, some crystals are virtually under no stress, whereas all the stress rests on others.

The creation of an integral assembly of zeolite crystals connected together via arches or bridges of the same nature, using a material prepared by agglomeration of crystals, increases the density of the network of "force chains" supporting all of the stresses, which thus considerably reinforces the mechanical strength of said zeolite material, giving it a rigidity similar to that of a material without porosity.

Thus, the zeolitic granular material of the invention comprises a macroporosity and a mesoporosity in which the liquid or gaseous phase circulates to transport the compounds to be separated by adsorption, from the exterior of the grain to the microporosity, and vice versa.

This macroporosity allows efficient transport from the exterior to the surface of the micropores and vice versa, without having to circulate through pores of smaller sizes: i.e. the macropores are the predominant pores for the transportation of the compounds to and from the micropores.

According to another aspect, the invention relates to a process for preparing zeolitic granular materials, as have just been defined, which process comprises at least the steps of:
a) mixing crystals of at least one zeolite with a clay binder containing at least 80%, preferably at least 90% and more preferably at least 95% by weight of zeolitizable clay, and optionally a source of silica,
b) placing in contact with an alkaline basic solution, typically a sodium hydroxide solution or a mixture of sodium hydroxide and potassium hydroxide, c) bringing the suspension to a temperature typically between 80° C. and 600° C., preferably between 80° C. and 150° C., in a closed and leaktight container, at a pressure at least equal to the autogenous pressure, typically between the autogenous pressure and 20 bar, d) optional cationic exchange of the cations contained in the reaction medium of step c) by placing in contact with a solution of barium ions, or of barium ions and potassium ions, e) washing and drying of the zeolitic granular materials thus obtained, and optionally at least one step of forming to the desired size, and f) activation by heating to a temperature in general between 100° C. and 400° C., preferably between 200° C. and 300° C., of the zeolitic granular material obtained in step e).

The size of the zeolite crystals in step a) and of the zeolite crystals in the granular materials is measured by observation with a scanning electron microscope (SEM), by taking a set of images at a magnification of at least 5000. The diameter of at least 200 crystals is then measured using dedicated image analysis software. The precision is of the order of 3%.

The crystals used in the context of the present invention preferably have a number-average diameter of less than or equal to 1.5 μm, preferably strictly less than 1.2 μm, and better still less than or equal to 1.1 μm.

As indicated previously, it is preferred to use zeolite crystals of faujasite structure with an Si/Al atomic ratio of between 1.00 and 1.50, preferably between 1.05 and 1.50 and even more preferably between 1.10 and 1.50, limits inclusive, measured by X-ray fluorescence chemical analysis.

During step a), besides the zeolite crystals and the clay, one or more additives may also be added, for example additives such as silica, especially in the case where the zeolite used is a zeolite X. The optional source of silica may be of any type known to a person skilled in the art, who is a specialist in zeolite synthesis, for example colloidal silica, diatomaceous earths, perlite, calcination ash (fly ash), sand, or any other form of solid silica.

The zeolite crystals used in step a) may thus be advantageously derived from the synthesis of zeolite X crystals predominantly or even exclusively comprising sodium cations, as is the case, for example, for NaX zeolites (or 13X), but it would not constitute a departure from the context of the invention to use crystals which have undergone one or more cationic exchanges, between the synthesis in NaX form and its use in step a). In this case, step d) of cationic exchange consequently becomes unnecessary.

The clay binder used in step a) contains at least 80%, preferably at least 90%, more preferably at least 95% and more particularly at least 96% by weight of clay or of mixture of clays from among kaolins, kaolinites, nacrites, dickites, halloysite and/or metakaolins and may also contain other mineral binders such as bentonite, attapulgite, sepiolite and the like.

The proportions of clays and zeolite(s) used are typically those of the prior art, i.e. from 5 parts to 20 parts by weight of clay(s) per 95 parts to 80 parts by weight of zeolite(s).

In any case, the clays may be used in their raw state or may be subjected beforehand to one or more treatments chosen, for example, from calcination, acid treatment, chemical modification and the like.

According to one embodiment, when the clay used is kaolin, baking of the mixture obtained in step a) is advantageously performed, before step b), at a temperature generally between 500° C. and 600° C. so as to convert the kaolin into meta-kaolin. The principle of this is outlined in *Zeolite Molecular Sieves* by D. W. Breck, John Wiley & Sons, New York, (1973), pp. 314-315.

Step b) of placing in contact with an alkaline basic solution is typically a step performed by immersing the mixture obtained in step a) in an alkaline basic solution, which is generally aqueous, for example an aqueous sodium hydroxide and/or potassium hydroxide solution. In general, the concentration of the alkaline solution of step b) is between 0.5 M and 5 M.

This step b) is performed cold or hot, preferably hot, at a temperature above room temperature, and typically between room temperature (i.e. about 20° C.) and the boiling point of the alkaline solution.

According to one characteristic of the process of the invention, this immersion is performed in a closed and leaktight container, so as to perform step c) under pressure, and typically under autogenous pressure. As a variant, an external pressurization means may be envisaged, and, in this case, the pressure will be between at least the autogenous pressure and 20 bar.

The activation that follows the drying is performed in a conventional manner, according to the methods known to those skilled in the art, for example at a temperature generally between 100° C. and 400° C., preferably between 200° C. and 300° C. The aim of this activation step f) is to set the water content and also the loss on ignition of the granular material at an optimum level for the envisaged use. This is generally performed by thermal activation, which is preferentially implemented at between 200° C. and 300° C. for a time determined as a function of the desired water content and loss on ignition, typically from 1 to 6 hours.

The process of the invention comprises, during step e), optionally at least one step of forming the zeolitic granular materials to the desired size, which may be performed according to any technique known to those skilled in the art, for instance a granulating plate, milling, crushing and the like, preferably crushing.

The process of the invention also comprises one or more optional forming steps which may be performed according to any technique known to those skilled in the art, for instance extrusion, compacting, agglomeration and the like. These forming steps may be performed after one or other or several of the steps a), b), c), d), e) or f). It is preferred to perform only one forming step after step a), b), c), d), e) or f), and preferably after step a), b), or c).

The forming step may optionally make use of an agglomeration binder. According to a preferred embodiment of the invention, said binder comprises at least 80% of a clay or a mixture of clays, which are optionally zeolitizable, and with up to 5% of additives and also with the amount of water for forming the agglomerated material. The zeolitic granular material may thus be formed into a bead, an extrudate or the like, with a size of between 0.1 mm and 1 mm, as indicated previously.

The zeolitic granular material according to the invention is particularly suited for processes for separating compounds in liquid phase, and especially for processes in which said material is subjected to large mechanical stresses, for example co-current or counter-current liquid-phase separation processes, and more particularly simulated mobile bed liquid-phase separation processes. The zeolitic granular material according to the invention is most particularly suited for processes for separating xylenes in liquid phase.

Thus, and according to yet another aspect, the present invention relates to the use of at least one zeolitic granular material, as has just been defined, as an adsorbent material in co-current or counter-current liquid-phase separation processes, and more particularly in simulated mobile bed liquid-phase separation processes, typically in processes for separating aromatic fractions comprising mixtures of aromatic isomers containing 8 carbon atoms and more particularly in liquid-phase processes for separating xylenes in a simulated mobile bed, and most particularly in processes for recovering high-purity para-xylene from aromatic isomer fractions containing 8 carbon atoms.

Finally, the invention also relates to the process for separating aromatic fractions comprising mixtures of isomers containing 8 carbon atoms and more particularly the liquid-phase process for separating xylenes in a simulated mobile bed, and most particularly the process for recovering high-purity para-xylene from aromatic isomer fractions containing 8 carbon atoms, as described, for example, in patent application WO 2009/081024, and in which is used at least one zeolitic granular material as described previously.

The examples that follow make it possible to illustrate the subject of the invention, and are given purely as a guide, without, however, being intended to limit in any way the various embodiments of the present invention.

The amount of zeolite fractions in the zeolitic granular material is measured by X-ray diffraction analysis, known to those skilled in the art by the abbreviation XRD. This analysis is performed on a Brüker brand machine, and the amount of zeolite fractions is then evaluated using the TOPAS software from the company Brüker.

The zeolitic granular material was evaluated as regards the Si/Al atomic ratio and the degree of cationic exchange by elemental chemical analysis of the zeolitic granular material, and more precisely by X-ray fluorescence chemical analysis as described in standard NF EN ISO 12677: 2011 on a wavelength-dispersive spectrometer (WDXRF), for example Tiger S8 from the company Brüker. The X-ray fluorescence spectrum has the advantage of being sparingly dependent on the chemical combination of the element, which affords a precise determination, which is both quantitative and qualitative. After calibration for each oxide $SiO_2$ and $Al_2O_3$, and also sodium, potassium and barium oxides, a measuring uncertainty of less than 0.4% by weight is conventionally obtained. The measuring uncertainty of the Si/Al atomic ratio is ±5%.

The determination of the size of the granular material is performed by analysis of the particle size distribution of an agglomerated sample by image analysis according to standard ISO 13322-2:2006, using a conveyor belt allowing the sample to pass in front of the camera objective lens. The size of the object (number-average diameter) is then calculated from the particle size distribution by applying standard ISO 9276-2:2001. The precision is of the order of 0.01 mm for the size range of the zeolitic granular material of the invention.

The macropore and mesopore volumes are measured by mercury intrusion porosimetry. An Autopore® 9500 mercury porosimeter from Micromeritics is used to analyze the distribution of the pore volume contained in the macropores and in the mesopores.

The experimental method, described in the machine's operating manual referring to standard ASTM D4284-83, consists in placing an adsorbent sample (zeolitic granular material to be measured) (known loss on ignition), weighed beforehand, in a porosimeter cell, and then, after degassing beforehand (vacuum pressure of 30 µmHg for at least 10 min), in filling the cell with mercury at a given pressure (0.0036 MPa), and then in applying a pressure increasing in stages up to 400 MPa so as to make the mercury gradually penetrate into the pore network of the sample.

The relationship between the applied pressure and the apparent pore diameter is established assuming cylindrical pores, a contact angle between mercury and the wall of the pores of 140° and a mercury surface tension of 485 dynes/cm. The cumulative amount of mercury introduced as a function of the applied pressure is recorded. The value at and above which the mercury fills all the inter-granular voids is set at 0.2 MPa and it is considered that above this value the mercury penetrates into the pores of the granular material. The grain volume (Vg) is then calculated by subtracting the cumulative volume of mercury at this pressure (0.2 MPa) from the volume of the porosimeter cell, and by dividing this difference by the mass of the anhydrous equivalent granular material, i.e. the mass of said material corrected for the loss on ignition.

The macropore volume of the granular material is defined as being the cumulative volume of mercury introduced at a pressure of between 0.2 MPa and 30 MPa, corresponding to the volume contained in the pores with an apparent diameter of greater than 50 nm. The mesopore volume of the granular material is defined as being the cumulative volume of mercury introduced at a pressure of between 30 MPa and 400 MPa.

In the present document, the macropore and mesopore volumes of the zeolite adsorbents, expressed in $cm^3.g^{-1}$, are thus measured by mercury intrusion and related to the anhydrous equivalent mass of the sample, i.e. the mass of said material corrected for the loss on ignition.

The micropore volume is determined according to any method known to those skilled in the art, for example from measurement of the adsorption isotherm of a gas at its liquefaction temperature, for example nitrogen, argon, oxygen and the like. Prior to this adsorption measurement, the zeolitic granular material of the invention is degassed at between 300° C. and 450° C. for a time of from 9 hours to 16 hours, under vacuum ($P<6.7\times10^{-4}Pa$). For example, for a zeolite of FAU structure, the measurement of the nitrogen adsorption isotherm at 77K is then performed on an ASAP 2010 M machine from Micromeritics, taking at least 35 measurement points at relative pressures of ratio $P/P_0$ of between 0.002 and 1. The micropore volume is determined according to the Dubinin-Raduskevitch equation from the isotherm obtained, by applying standard ISO 15901-3:2007. The micropore volume thus evaluated is expressed in $cm^3$ of liquid adsorbate per gram of adsorbent. The measuring uncertainty is ±0.003 $g/cm^3$.

The measured mechanical strength is the bulk crushing strength (BCS) characterized according to the Shell method series SMS1471-74 (Determination of Bulk Crushing Strength of Catalysts. Compression-Sieve Method), associated with the BCS Tester machine sold by the company Vinci Technologies.

This method for measuring the BCS, initially intended for the characterization of catalysts of 3 mm to 6 mm, is based on the use of a 425 µm screen which makes it possible especially to separate the fines created during crushing. The use of a 425 µm screen remains suitable for particles with a diameter of greater than 1.6 mm but must be adapted according to the particle size of the material that it is desired to characterize. For the zeolitic granular material of the present invention, a 200 µm screen is used instead of the 425 µm screen mentioned in the Shell method standard SMS1471-74.

The measuring protocol is as follows: a sample of 20 $cm^3$ of material to be analyzed, screened beforehand with the appropriate screen (200 µm) and dried beforehand in an oven for at least 2 hours at 250° C. (instead of 300° C.

mentioned in the Shell method standard SMS1471-74), is placed in a metal cylinder of known inside cross section. An increasing force is imposed in stages on this sample by means of a piston, through a bed of 5 cm³ of steel balls so as to better distribute the force exerted by the piston on the material (use of balls 2 mm in diameter for particles of spherical form with a diameter strictly less than 1.6 mm). The fines obtained at the various pressure stages are separated by screening (appropriate screen of 200 μm) and weighed.

The BCS is determined by the pressure in megapascals (MPa) for which the cumulative amount of fines passing through the screen is 0.5% by weight of the sample. This value is obtained by plotting on a graph the mass of fines obtained as a function of the force applied to the bed of zeolite material and by interpolating to 0.5% by mass of cumulative fines. The mechanical bulk crushing strength is typically between a few hundred kPa and a few tens of MPa and generally between 0.3 MPa and 3.2 MPa. The precision is conventionally less than 0.1 MPa.

The attached figures are images obtained during observation by scanning electron microscopy (SEM) of a polished section of various zeolitic granular materials. The polished surface of the material was prepared by ionic polishing (argon ion). The machine used for the preparation is an Ilion+™ machine sold by Gatan, with the following parameters: acceleration voltage of 5 kV, polishing time of 4 hours, tilt angle 0°, room temperature, cross-section mode.

For the observation of the sample, a field-emission gun scanning electron microscope (FEG SEM) is used under the following conditions: acceleration voltage of 2 kV, image analysis with an Everhart-Thornley lateral secondary electron detector, magnification reference Polaroid 545. The sample was not subjected to metalization.

The examples that follow make it possible to illustrate the subject of the invention. They are given purely as a guide, and are not intended to limit in any way the various embodiments of the present invention.

EXAMPLE 1 (COMPARATIVE)

Preparation of a Non-Connected Material Based on NaX

A zeolite adsorbent is prepared based on zeolite X powder with a crystal size of 1 μm of atomic ratio Si/Al=1.25, obtained by intimately mixing and agglomerating 100 g (expressed as calcined equivalent) of zeolite NaX powder with a crystal size of 1 μm and an atomic ratio Si/Al=1.25 with 15 g of kaolin (expressed as calcined equivalent) and 7.5 g of colloidal silica sold under the trade name Klebosol®30 (containing 30% by weight of $SiO_2$ and 0.5% of $Na_2O$) with the amount of water suitable for working by extrusion.

The adsorbents are dried, crushed so as to recover grains whose number-average equivalent diameter is equal to 0.5 mm, and then calcined at 550° C. under a stream of nitrogen for 2 hours.

In this step, an observation of a polished section of the material according to the invention is performed by SEM: on ten images with a magnification of 10 000, an agglomerate of zeolite crystals is observed, such that the crystals do not form a connected assembly over the entire volume of said material, the connected surface representing about 5% of the surface occupied by the material in the image (FIG. 1a).

The mechanical bulk strength BCS of these agglomerates measured as described above is 0.8 MPa. The proportion of the mesopores by volume relative to the total volume of macropores and mesopores is $$0.13\left(\frac{Vme}{Vme+Vma}=0.13\right),$$

the proportion of micropore volume relative to the sum of the macropore, mesopore and micropore volumes is $$0.60\left(\frac{Vmi}{Vma+Vme+Vmi}=0.60\right),$$

and the proportion of the mesopore and macropore volumes relative to the total volume of the granular material is $$0.39\left(\frac{Vma+Vme}{Vg}=0.39\right).$$

EXAMPLE 2 (ACCORDING TO THE INVENTION)

Synthesis of a Connected Zeolite Material Based on NaX

A zeolite adsorbent as prepared in Example 1 is used.

These dried and calcined extrudates are placed in contact with a basic solution prepared by mixing 200 g of sodium hydroxide (NaOH at 50% by weight in water) with 300 g of water with gentle stirring. The mixture is then transferred into plastic tubes which are then sealed. The system is maintained at a temperature regulated at 120° C. for 2 hours under autogenous pressure.

The adsorbents are recovered and then washed with water until the pH is close to 10. The extrudates are dried, crushed so as to recover grains with a number-average equivalent diameter equal to 0.5 mm, and then calcined at 550° C. under a stream of nitrogen for 2 hours.

The adsorbent in this step is observed by SEM on polished sections prepared by ionic polishing. The observation of ten images taken on different polished sections, with a magnification of 10 000, shows a homogeneous porosity and a homogeneous material. Analysis of the SEM images shows, on average out of the ten images, a connected surface representing about 78% of the surface occupied by the material on each image, which corresponds to a connected material within the meaning of the invention.

The reinforcement of the mechanical strength is moreover observed during polishing under the conditions described, via a curtain effect (groove observed in FIG. 2a or FIG. 2b), characteristic of a hard material. This effect is absent during the polishing of the material represented in FIG. 1a or FIG. 1b, which is an agglomerate of zeolite crystals, such that the crystals do not form a connected assembly.

The mechanical bulk strength BCS of these agglomerates measured as described above is 2.5 MPa. The volume proportion of the mesopores relative to the total macropore and mesopore volume is $$0.05\left(\frac{Vme}{Vme+Vma}=0.05\right),$$

the proportion of micropore volume relative to the sum of the macropore, mesopore and micropore volumes is $$0.52 \left( \frac{Vmi}{Vma + Vme + Vmi} = 0.52 \right),$$

and the proportion of the mesopore and macropore volumes relative to the total volume of the granular material is $$0.32 \left( \frac{Vma + Vme}{Vg} = 0.32 \right).$$

EXAMPLE 3 (ACCORDING TO THE INVENTION)

Synthesis of a Connected Zeolite Material Based on BaX 50 g of sodium hydroxide at 50% by weight in water, 20 g (expressed as anhydrous equivalent) of zeolite NaX powder with a crystal size of 0.8 μm and an Si/Al atomic ratio=1.20, 1 g of kaolin (expressed as calcined equivalent) calcined beforehand at 550° C. for 2 hours and 0.5 g of colloidal silica sold under the trade name Klebosol®30 (containing 30% by weight of $SiO_2$ and 0.5% of $Na_2O$) are mixed with 25 g of water in a container.

The mixture thus obtained is transferred into plastic tubes which are then sealed. The system is maintained at a temperature regulated at 120° C. for 2 hours under autogenous pressure.

The adsorbents are recovered and then washed with water until the pH is close to 10. The extrudates are dried, crushed so as to recover grains with a number-average equivalent diameter equal to 0.5 mm, and then calcined at 550° C. under a stream of nitrogen for 2 hours.

These adsorbents are subjected to a cationic exchange via the action of an aqueous 0.5 M barium chloride solution at 95° C. in 4 steps. At each step, the volume ratio of solution to the mass of solid is 20 mL/g and the exchange is continued for 4 hours each time. Between each exchange, the solid is washed several times so as to free it of the excesses of salt. The agglomerates are then dried at 80° C. for 2 hours and finally activated at 250° C. for 2 hours under a stream of nitrogen.

The mechanical bulk strength BCS of these agglomerates measured as described above is 2 MPa. The volume proportion of the mesopores relative to the total macropore and mesopore volume is $$0.08 \left( \frac{Vme}{Vme + Vma} = 0.08 \right),$$

the proportion of micropore volume relative to the sum of the macropore, mesopore and micropore volumes is $$0.53 \left( \frac{Vmi}{Vma + Vme + Vmi} = 0.53 \right),$$

and the proportion of the mesopore and macropore volumes relative to the total volume of the granular material is $$0.33 \left( \frac{Vma + Vme}{Vg} = 0.33 \right).$$

The invention claimed is:

1. A zeolitic granular material having a particle size of from 0.1 mm to 1 mm, wherein
   the zeolitic granular material has a mechanical bulk crushing strength of greater than or equal to 1.0 MPa,
   the zeolitic granular material contains a zeolite structure that has a three-dimensionally connected surface,
   the proportion of connected surface represents at least 50% of the surface occupied by the zeolitic granular material when ten images of polished sections of the zeolitic granular material are examined with a scanning electron microscope at a magnification of from 5,000 to 10,000,
   the zeolitic granular material comprises at least one zeolite selected from the group consisting of zeolite LSX, zeolite MSX and zeolite X, and
   the pore distribution satisfies the inequalities 1), 2) and 3) below:

$$\frac{Vme}{Vme + Vma} \leq 0.1; \quad\quad 1)$$

$$0.4 \leq \frac{Vmi}{Vma + Vme + Vmi}; \quad\quad 2)$$

and $$0.25 \leq \frac{Vma + Vme}{Vg} \leq 0.35; \quad\quad 3)$$

wherein
   Vma represents the macropore volume,
   Vme represents the mesopore volume,
   Vmi represents the micropore volume, and
   Vg represents the total volume of the granular material.

2. The zeolitic granular material of claim 1, comprising more than 94% by weight of zeolite(s), relative to the total weight of the zeolitic granular material.

3. The zeolitic granular material of claim 1, wherein $$0.01 \leq \frac{Vme}{Vme + Vma} \leq 0.1.$$

4. The zeolitic granular material of claim 1, wherein $$0.01 \leq \frac{Vme}{Vme + Vma} \leq 0.06.$$

5. The zeolitic granular material of claim 1, wherein $$0.4 \leq \frac{Vmi}{Vma + Vme + Vmi} \leq 0.6.$$

6. The zeolitic granular material of claim 1, wherein $$0.45 \le \frac{Vmi}{Vma + Vme + Vmi} \le 0.55.$$

7. The zeolitic granular material of claim 1, having a size between 0.3 mm and 0.8 mm, limits inclusive.

8. The zeolitic granular material of claim 1, having a mechanical bulk crushing strength greater than or equal to 2.0 MPa.

9. The zeolitic granular material of claim 1, comprising zeolite X.

10. The zeolitic granular material of claim 1, comprising between 96% and 98% by weight of zeolite(s), limits inclusive, relative to the total weight of the zeolitic granular material.

11. A process for preparing the zeolitic granular material of claim 1, comprising:
   a) mixing crystals of at least one zeolite with a clay binder containing at least 80% by weight of zeolitizable clay, and, optionally, a source of silica to form a mixture,
   b) placing the mixture in contact with an alkaline basic solution to form a suspension,
   c) bringing the suspension to a temperature between 80° C. and 600° C., in a closed and leaktight container, at a pressure at least equal to the autogenous pressure to obtain a zeolitic granular material,
   d) optionally, carrying out cationic exchange of the cations contained in the reaction medium of step c) by placing the reaction medium in contact with a solution of barium ions, or of barium ions and potassium ions,
   e) washing and drying of the zeolitic granular material thus obtained, and, optionally, at least one step of forming the zeolitic granular material to a desired size, and
   f) activating the zeolitic granular material obtained in e) by heating to a temperature between 100° C. and 400° C.

12. The process of claim 11, wherein the clay binder contains at least 80% by weight of clay, wherein the clay comprises at least one member selected from the group consisting of kaolins, kaolinites, nacrites, dickites, halloysite and metakaolins, and wherein the clay binder may optionally comprise at least one other mineral binder.

13. A process for separating aromatic fractions comprising mixtures of isomers containing 8 carbon atoms, comprising contacting an aromatic fraction comprising mixtures of isomers containing 8 carbon atoms with the zeolitic granular material of claim 1.

14. The process of claim 13, wherein the process is a liquid-phase process for separating xylenes in a simulated mobile bed.

15. The process of claim 13, wherein the aromatic fraction contains xylenes.

* * * * *